United States Patent [19]

Birum

[11] 4,086,205

[45] Apr. 25, 1978

[54] HYDROGEN PHOSPHONATES

[75] Inventor: Gail H. Birum, Kirkwood, Mo.

[73] Assignee: Monsanto Company, St. Louis, Mo.

[21] Appl. No.: 720,324

[22] Filed: Sep. 3, 1976

[51] Int. Cl.$^2$ .................. C07F 9/38; C08K 5/17; C08K 5/18

[52] U.S. Cl. ................ 260/45.8 R; 260/927 R

[58] Field of Search .................. 260/45.8 R, 927 R

[56] References Cited

U.S. PATENT DOCUMENTS

| | | | |
|---|---|---|---|
| 2,957,856 | 10/1960 | Guest et al. | 526/225 |
| 3,413,382 | 11/1968 | Ulrich | 260/937 |
| 3,887,655 | 6/1975 | Shim | 260/937 |
| 3,966,849 | 6/1976 | Noetzel et al. | 260/45.8 R |
| 3,978,167 | 8/1976 | Albright | 260/927 R |
| 3,997,505 | 12/1976 | Albright | 260/45.8 R |
| 4,007,236 | 2/1977 | Duffy et al. | 260/927 R |

OTHER PUBLICATIONS

Sehring – Chem. Abs. 79, 115722k, (1973).

*Primary Examiner*—Melvyn I. Marquis
*Assistant Examiner*—H. H. Fletcher
*Attorney, Agent, or Firm*—Herman O. Bauermeister

[57] ABSTRACT

The present invention relates to cyclic phosphorus compounds and processes for the preparation thereof.

The present invention relates to a process for the preparation of certain derivatives of cyclic hydrogenphosphonates which are diisocyanate derivatives formed as adducts or as polymers.

The cyclic phosphorus compounds are useful as flame retardants with organic polymers, such as polyurethanes, polyesters, and polyamides.

9 Claims, No Drawings

HYDROGEN PHOSPHONATES

BACKGROUND OF THE INVENTION

The present invention relates to cyclic phosphorus compounds, such as certain cyclic hydrogen phosphonate derivatives, processes for the preparation of such compounds and their derivatives and to flame retardant compositions containing the said cyclic phosphorus compounds.

Certain phosphonates have been employed as flame retardant additives, but have suffered from the defect of causing undesirable crosslinking of polymeric materials in which the phosphonates were employed. For example, the addition of such phosphonates to a molten polymer such as polyethylene terephthalate or a nylon, preliminary to the extrusion or spinning step has shown that the crosslinking prevents the formation of acceptable fibers. As a result of the crosslinking, the fibers contain lumps and irregular sections so that the extrusion through spinnerettes is hampered and the stretching, washing and other physical treatments of the fiber become impossible.

It has now however been found that certain cyclic phosphorus compounds including cyclic phosphonates are particularly useful as flame retardants for organic polymeric materials. The invention includes combinations of the present cyclic phosphorus compounds together with organic polymers such as polyurethanes, polyesters, e.g. polyethylene terephthalate, and polyamides e.g., the nylons.

SUMMARY OF THE INVENTION

The general formulae for the cyclic phosphorus derivatives of the invention are:

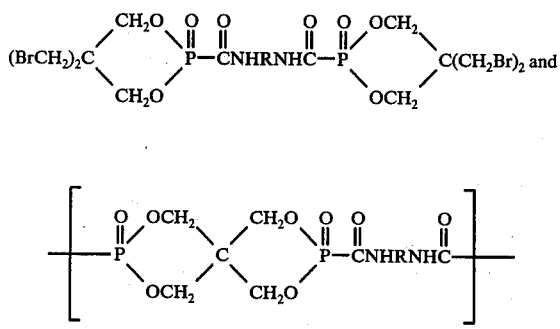

where R is selected from the group consisting of alkylene or alkyl substituted alkylenes of 2 to 20 carbon atoms, or arylene and alkyl substituted arylenes of 6 to 22 carbon atoms. The polymer has a degree of aggregation of 2 to 100.

The above compounds are derivatives of cyclic hydrogen-phosphonates. They are obtained by the reaction of a crude or purified hydrogen phosphonate with a diisocyanate.

Representative examples of diisocyanates are 4,4'-diphenylmethane diisocyanate; butylene diisocyanate; propylenediisocyanate; octadecylene diisocyanate; hexamethylene diisocyanate; tolylene-2,4-diisocyanate; isophorone diisocyanate; and 2,2,4-(2,4,4-) trimethylhexamethylene diisocyanate.

The general reactions for the preparation of the diisocyanate derivatives as adducts (first equation based upon mono hydrogen phosphonates as reactants), or as polymers (second equation based upon dihydrogen phosphonates) are:

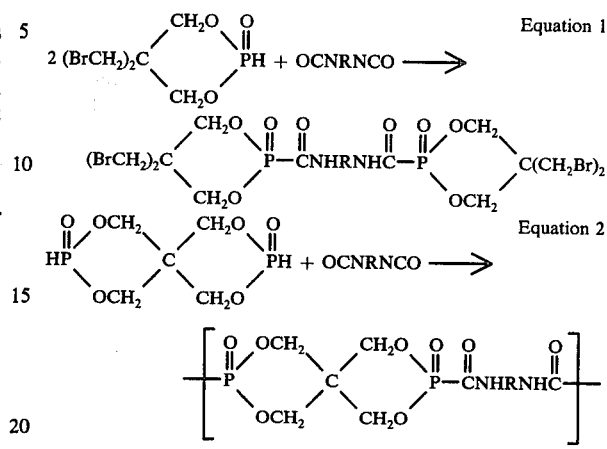

where R is the same as above. Examples of R include butylene, phenylene, and tolylene.

The present cyclic phosphorus compounds of the invention, existing as adducts or polymers are useful per se as flame retardant materials which provide phosphorus as a component to reduce flammability. Improvement in flame retardant properties result when the present derivatives are used with organic polymers. Such resultant products do not burn readily, and instead inhibit flammability of an organic polymer, for instance a polyurethane which is useful in the production of an elastomer or a rigid or flexible foam. An example of an elastomeric polyurethane is the product obtained by heating together poly(tetramethylene ether)glycol and methylene bis(p-phenylisocyanate).

The cyclic phosphorus compounds including the cyclic hydrogen phosphonates of the present invention are useful as flame retardant modifiers for organic polymers. These compounds can be added directly to the molten polymer or the components of a foam composition before polymerization, e.g. before spinning fibers or forming films or other shaped objects including foamed plastics. Typical polymers are polyesters, polyamides, polyurethanes, polyolefins, nitrile polymers such as polyacrylonitrile, vinyl polymers such as vinyl chloride, styrene polymers and copolymers such as acrylonitrile-butadiene-styrene compositions.

The general reaction of the process for the production of hydrogen phosphonates that are useful in the practice of the present invention is based upon the use of formic acid with a cyclic phosphorohalidite, such as a phosphorochloriditе, represented in the process below by the structure,

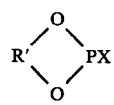

where R' is an alkylene, or haloalkylene group of a 1,2-glycol having from 2 to 8 carbon atoms, or of a 1,3 glycol having from 3 to 8 carbon atoms, and X is Cl or Br. An example is:

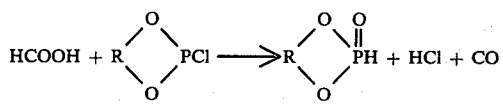

Examples of specific useful phosphorochloridites are the bis-(phosphorochloridites), such as 3,9-dichloro-2,4,8,10-tetraoxa-3,9-diphosphaspiro[5.5]undecane,

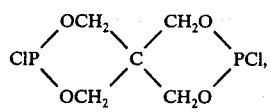

and the corresponding bromo derivative; 2-chloro-5,5-bis(bromomethyl)-1,3,2-dioxaphosphorinane,

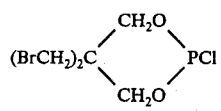

and the related phosphorochloridites, 2-chloro-5,5-dimethyl-1,3,2-dioxaphosphorinane, and 2-chloro-5-ethyl-5-methyl-1,3,2-dioxaphosphorinane, and 2-bromo-5,5-bis(chloromethyl)-1,3,2-dioxaphosphorinane, and 2-chloro-5-phenyl-1,3,2-dioxaphosphorinane, and 2-chloro-5-(4-fluoro-3-bromophenyl)-1,3,2-dioxaphosphorinane.

The process of converting cyclic phosphorochloridites to cyclic hydrogen phosphonates can also be applied to five-membered ring phosphorochloridites, e.g., 4,5-dimethyl-2-chloro-1,3,2-dioxaphospholane, 2-chloro-1,3,2-dioxaphospholane, 2-butyl-1,3,2-dioxaphospholane, 4-chloromethyl-1,3,2-dioxaphospholane, and 4-methyl-1,3,2-dioxaphospholane.

The method of treating cyclic phosphorochloridites with formic acid provides an improved process for producing cyclic hydrogenphosphonates, sometimes called cyclic phosphites. Some earlier workers in this area of phosphorus chemistry have also called these compounds cyclic hydrogen phosphites, but preferable general terminology is to call these compounds cyclic hydrogenphosphonates because it better describes the predominant pentavalent state of the phosphorus. A number of methods are known for preparing cyclic hydrogenphosphonates, such as the use of triethylamine as an acid-binding agent in the hydrolysis of cyclic chlorophosphites (cyclic phosphorochloridites). In this procedure, an amine hydrochloride is produced as a by-product, and this must then be separated from the desired cyclic hydrogenphosphonate.

In the above process, using formic acid instead of water, the by-products are anhydrous hydrogen chloride and carbon monoxide, gaseous products which are easily removed, leaving the easily isolated cyclic hydrogenphosphonate. For example, when attempts were made to prepare 3,9-H-3,9-dioxo-2,4,8,10-tetraoxa-3,9-diphosphaspiro[5.5]undecane(I),

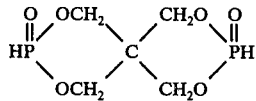

(I)

by treatment of 3,9-dichloro-2,4,8,10-tetraoxa-3,9-diphosphospiro[5.5]undecane with water by the prior art procedures, none of the desired product could be isolated from the mixture of side reaction products. However, when formic acid is used according to the present invention, essentially pure and easily isolated compound I is obtained.

Catalysts are unnecessary in the above process for preparing hydrogen phosphonates. A solvent is generally unnecessary when formic acid is used for conversion of cyclic phosphorochloridites to cyclic hydrogenphosphonates. Inert solvents or suspending liquids, e.g. acetonitrile, benzene, and 1,2-dichloroethane, can however be used to aid mixing and temperature control.

The reaction is usually carried out by the addition of formic acid to the stirred phosphorochloridite at 10° to 100° C, preferably 30° to 70° C, while allowing the by-products hydrogen chloride (or hydrogen bromide) and carbon monoxide to be expelled through a condenser and then trapped or absorbed by suitable and safe methods such as neutralization. In one case, this mixture of gases is passed into a stirred suspension of aluminum trichloride and toluene to produce p-tolualdehyde by the Gatterman-Koch Reaction, thus confirming the composition of the effluent gases and demonstrating a practical by-product recovery application.

The process for the preparation of the said derivatives as adducts, or polymers by treating a hydrogenphosphonate with a diisocyanate is carried out at 0° C to 100° C. No solvent is necessary, although inert solvents such as benzene, toluene and chlorobenzene may be used.

For this process, a basic catalyst is desirable. Examples of typical useful basic catalysts are, e.g. the heterocyclic nitrogen bases such as N-methylmorpholine, pyridine, quinoline, N-ethylpiperidine, picoline, quinaldine, 4-methylpyrimidine, or N-phenylpyrazole; the tertiary amines such as triethylamine, trimethylamine, tri-tert-butylamine, N,N-dimethylaniline and N-benzyl-N-methylaniline; alkylene polyamines such as triethylenediamine; quaternary ammonium compounds such as benzyltrimethylammonium methoxide or tetrabutylammonium butoxide; alkali metal alkoxides such as sodium or potassium methoxide, etc. The quantity of catalyst to be used will depend upon the nature of the specific disocyanate and cyclic hydrogenphosphonate; obviously the more reactive reactants will require less catalysts than will the somewhat more sluggish reaction compounds. Whether or not a diluent is used will likewise regulate catalyst quantity. Also variable is the temperature at which reaction is effected; for, here again must be taken into consideration the nature of the reactants, catalyst quantity, and whether or not a diluent is used. The reaction is generally exothermic; hence the present addition reactions can be conducted at ordinary room temperature or even at decreased temperatures, but heating of the reaction mixture may be needed to complete the reaction. All of these variables, i.e. catalyst quantity, use of diluent and temperature conditions can readily be arrived at by easy experimentation.

The compounds of the present invention are useful in flame-retardant materials. The method of testing flame-retardant properties is A.S.T.M. Designation D 2863-70, entitled "Standard Method of Test for Flammability of Plastics Using the Oxygen Index Method."

In the oxygen index (OI) testing procedure the relative flammability of a plastic material such as nylon, or polyethylene terephthalate is determined by measuring the minimum concentration of oxygen in a slowly rising mixture of oxygen and nitrogen that will just support combustion. Consequently the oxygen index expresses such minimum concentration of oxygen, expressed as volume percent, in a mixture of oxygen and nitrogen that will just support combustion.

The test is conducted by burning the material in a test column which is a heat resistant glass tube of 75 mm minimum inside diameter and 450 mm minimum height. At the bottom of the tube is a bed of glass beads about 100mm deep to mix and distribute the gas mixture. Within the glass tube used as the test column there is a specimen holder to support the treated plastic material while the apparatus is supplied with oxygen and nitrogen flow and control devices. The apparatus is also provided with an igniter which is a separate tube through which a combustible gas such as natural as is used to ignite the test specimen. In the present testing program glass scrim supported molded sheets of nylon or polyethylene terephthalate ca. 0.2mm thick and about 25mm by 100mm in size are used as the test specimens which are prepared from nylon or polyethylene terephthalate powder and 1% to 20° by weight of the fire retardant additive; the data in the present work correspond to about 10% by weight of additive. As a result of the molding of the organic polymer, e.g. nylon or polyethylene terephthalate, and the additive, and intimate admixture or melt of the molecules of the components is obtained.

In conducting the test, the specimen is clamped in the holder in the test column after which the desired initial concentration of oxygen is introduced to the ignited specimen. A number of tests are conducted to determine the minimum concentration of oxygen that will just support combustion.

The present condensation products are useful in combination with organic polymers generally to reduce combustibility. The normally flammable organic polymers which are rendered fire retardant in accordance with the invention may be natural or synthetic but are preferably a solid synthetic polymer, more preferably a nylon or ester type polymer. Examples of the polymers are cotton, wool, silk, paper, natural rubber, and paint, and also the high molecular weight homopolymers and copolymers of amides, e.g., (nylon 66 and nylon 6). Other polymers include esters such as polyethylene terephthalate, and polymers of other unsaturated aliphatic and aromatic hydrocarbons, e.g. ethylene, propylene, butylene, styrene, etc., and also acrylic polymers, e.g., polyacrylonitrile, polymethyl methacrylate, alkyd resins, as well as cellulose derivatives, e.g., cellulose acetate, methyl cellulose, etc. Still other polymers include epoxy resins, furan resins, isocyanate resins such as polyurethanes, melamine resins, vinyl resins such as polyvinyl acetate and polyvinyl chloride, resorcinol resins, synthetic rubbers such as polyisoprene, polybutadiene-acrylonitrile copolymers, butadiene-styrene polymers, butyl rubber, neoprene rubber, ABS resins and mixtures thereof. Since the compositions of the invention are unusually effective flame retardants they are normally combined in flame retarding proportions with the organic polymer at relatively low concentrations, e.g., about 1-20 wt. %, preferably about 3-15% based on additive plus the polymeric substrate, such as by milling, or impregnation, e.g., from a water or alcohol dispersion or solution or by dissolving or dispersing in the molten polymer before extrusion such as in the form of fibers or sheets. It should be noted that it is within the scope of the invention to incorporate such ingredients as dyes, pigments, stabilizers, antioxidants, antistatic agents and the like into the novel compositions.

The cyclic phosphorus compounds of the invention have a lesser tendency to cause cross linking than prior phosphonate flame retardants.

The following examples illustrate embodiments of the invention but are not restrictive.

EXAMPLE 1

A reaction vessel is charged with 272 grams (2.0 moles) of pentaerythritol, 567 grams of phosphorus trichloride, 0.1 gram of pyridine hydrochloride, and 272 grams of ortho-dichlorobenzene as a solvent. This mixture is warmed to 100° C in 2 hrs. and kept at 100°–105° C for one hour, giving a clear, colorless solution having a $^{31}P$ nmr signal at $-149$ ppm for the cyclic phosphorochloridite, 3,9-dichloro-2,4,8,10-tetraoxa-3,9-diphosphaspiro[5.5]undecane. This intermediate is converted to the hydrogenphosphonate by dropwise addition of 184 grams (4 moles) of 97–100% formic acid over a 65 minute period. The temperature is maintained at about 25°–42° C during the addition. A stream of gaseous nitrogen is passed through the stirred reaction mixture until most of the by-product HCl and CO have been swept out. The reaction mixture is filtered to remove solids which are then washed with benzene, followed by acetonitrile and ether. The white solid product, $^{31}P$ nmr-6.4(d, $J_{PH}=696$ cps), is 3,9-H-3,9-dioxa-2,4,8,10-tetraoxa-3,9-diphosphaspiro[5.5]undecane having the formula shown below:

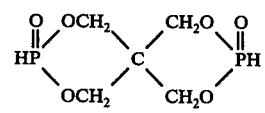

Analysis: Calcd. for $C_5H_{10}O_6P_2$(percent): C, 26.33; H, 4.42; P, 27.16. Found: C, 26.17; H, 4.76; P, 26.77.

The use of $PBr_3$ instead of $PCl_3$ leads to the same product.

EXAMPLE 2

Phosphorus trichloride, 274.8 g (2.0 moles), is added dropwise to a stirred solution of 524g. (2.0 moles) of 2,2-di(bromomethyl)-1,3-propanediol and 0.2g. of pyridine hydrochloride in 600 g. of benzene during 2.5 hrs. with enough warming to keep the temperature above 20° C. After several hours of stirring at room temperature, a $^{31}P$ nmr spectrum of the reaction mixture shows a peak for 90% of the phosphorus at $-146.6$ ppm for 2-chloro-5,5-di(bromomethyl)-1,3,2-dioxaphosphorinane.

Stirring of the reaction mixture is continued as 106 g. (2.3 moles) of formic acid is added at room temperature during 2 hrs., followed by warming at 45° C. for 1.5 hrs. A solid product separates on cooling. This is recrystallized from benzene, giving 333 g. of white solid, m.p. 91°–96°, $^{31}P$ nmr $-5.2$ ppm (d, $J_{PH}=695$ cps), which is the cyclic hydrogenphosphonate, 5,5-bis(bromomethyl)-2-H-2-oxo-1,3,2-dioxaphosphorinane, having the structure,

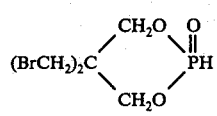

EXAMPLE 3

A mixture of 0.1 mole of the product of Example 2 and 0.05mole of 1,6-diisocyantohexane in 100 g. of benzene is stirred as 30 drops of triethylamine is added at 23°–32° C. The reaction mixture is warmed at 50°–60° for 0.5 hr. and then filtered. The solid product is washed with warm benzene and acetone, giving 31.3g of white solid, m.p. 198°–206°, $^{31}$P nmr 8.5 ppm, which is 5,5,5',5'-tetrakis(bromomethyl)-N,N'-hexamethylene-bis(2,2'-dioxo-1,3,2-dioxaphosphorinane-2-carboxamide),

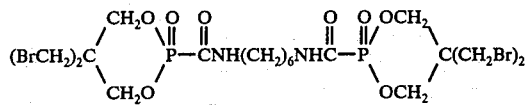

Analysis — Calcd. for $C_{18}H_{30}Br_4N_2O_8P_2$: C, 27.57; H, 3.86; Br, 40.76; N, 3.57; P, 7.90. Found: C, 27.89; H, 3.69; Br, 41.08; N, 3.57; P, 7.85.

EXAMPLE 4

Similarly, 0.1 mole of the product of Example 2 and 0.05mole of tolylene-2,4-diisocyanate gives 33.5 g. of white solid, m.p. 199°–210° C, $^{31}$P nmr 8.9 ppm, which is 5,5,5',5'-tetrakis(bromomethyl)-N,N'-(o-methylphenylene)-bis(2,2'dioxo-1,3,2-dioxaphosphorinane-2-carboxamide).

Analysis — Calcd. for $C_{19}H_{24}Br_4N_2O_8P_2$: C, 28.89; H, 3.06; Br, 40.46; N, 3.55; P, 7.84. Found: C, 28.54; H, 3.03; Br, 39.94; N, 3.50; P, 7.72.

Other examples of diisocyanates that give analogous cyclic phosphorus adducts are 4,4'-diphenylmethane diisocyanate; butylene diisocyanate; propylene diisocyanate; octadecylene diisocyanate; hexamethylene diisocyanate; isophorone diisocyanate and 2,2,4-(2,4,4-)trimethylhexamethylene diisocyanate.

EXAMPLE 5

A mixture of 0.1 mole of the product of Example 1 and 0.1 mole of hexamethylenediisocyanate in 200 ml of dimethylformamide is stirred as 40 drops of triethylamine is added. A mildly exothermic reaction occurs, causing a temperature rise from 24° to 32° C. The reaction mixture is warmed at 70°–80° for 0.5 hr, and then 250 ml of acetonitrile is added in 10 minutes, causing a white polymer to separate. The mixture is warmed at 75° for 1 hr, and then it is filtered while hot. The white solid is extracted with hot acetonitrile and acetone and dried at 100°/0.15 mm, giving 31.1 g. of white powder which is a polymer having the structure,

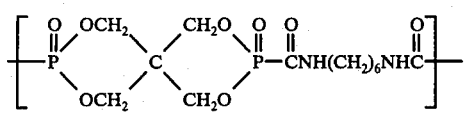

It can be molded at 230°–240° C and 20,000 psi.

EXAMPLE 6

Similarly to the preceding example, a polymer is prepared from 0.1 mole each of the product of Example 1 and tolylene-2,4-diisocyanate in dimethylformamide using triethylamine as a catalyst to promote polymerization.

Other examples of diisocyanates that give analogous cyclic phosphorus polymers are 4,4'-diphenylmethane diisocyanate; butylene diisocyanate; propylene diisocyanate; octadecylene diisocyanate; tolylene-2,4-diisocyanate; isophorone diisocyanate and 2,2,4-(2,4,4-) trimethylhexamethylene diisocyanate.

EXAMPLE 7

Flame retardancy tests are conducted using typical compounds of the invention, specifically the compounds of the above examples. These compounds do not burn readily when subjected to heat and a flame; they also improve the flame retardant properties of polyamides, specifically nylon-6,6 and of polyethylene terephthalate, at concentrations of 1–20% by weight, preferably 3–15% by weight, based upon the total mixture, obtained such as by milling, or impregnation or by dissolving or dispersing in the polymer in molten form before extrusion such as in the form of fibers or sheets. It should be noted that it is within the scope of the invention to incorporate such ingredients as dyes, pigments, stabilizers antioxidants, antistatic agents, and the like into the novel compositions.

Test data of the oxygen index test described above for certain compounds are set forth below:

| Compound of Example | O-I Value (10% additive) |
|---|---|
| 3 | 25.3 |
| 4 | 25.2 |
| 5 | 23.0 |
| 6 | 25.3 |

The present diisocyanate derivatives, as a group have flame retardant properties for polyethylene terephalate and polyamides such as nylon 6,6.

What is claimed is:

1. A cyclic phosphorus composition

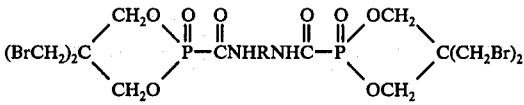

where R is selected from the group consisting of alkylene and alkyl substituted alkylenes of 2 to 20 carbon atoms, or is selected from the group consisting of arylene and alkyl substituted arylenes of 6 to 22 carbon atoms.

2. A cyclic phosphorus composition

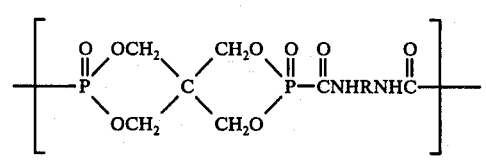

with —H and —NCO end groups, and having a degree of aggregation of 2 to 100, where R is selected from the group consisting of alkylene and alkyl substituted alkylenes of 2 to 20 carbon atoms, or is selected from the group consisting of arylene and alkyl substituted arylenes of 6 to 22 carbon atoms.

3. The composition of matter

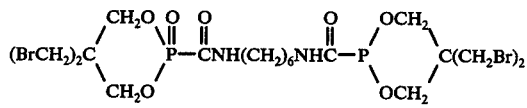

4. The composition of matter

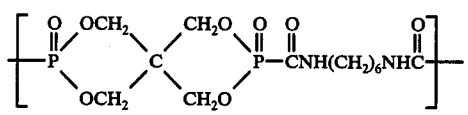

with —H and —NCO end groups, and having a degree of aggregation of 2 to 100.

5. Process for preparing a cyclic phosphorus composition which comprises admixing formic acid with a cyclic phosphorochloridite, having the formula

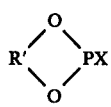

where R' is an alkylene, or a haloalkylene group of a 1,2-glycol having from 2 to 8 carbon atoms, or of a 1,3-glycol having from 3 to 8 carbon atoms, and X is Cl or Br, at 10°–100° C and thereafter treating the resulting intermediate with a diisocyanate.

6. The combination of an organic polymer together with

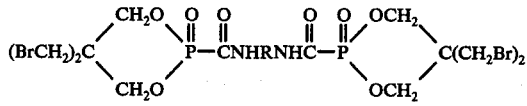

where R is selected from the group consisting of alkylene and alkyl substituted alkylenes of 2 to 20 carbon atoms, or is selected from the group consisting of arylene and alkyl substituted arylenes of 6 to 22 carbon atoms.

7. The combination of an organic polymer together with

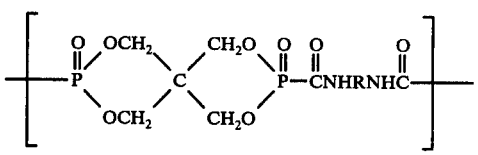

with —H and —NCO end groups, and having a degree of aggregation of 2 to 100, where R is selected from the group consisting of alkylene and alkyl substituted alkylenes of 2 to 20 carbon atoms, or is selected from the group consisting of arylene and alkyl substituted arylenes of 6 to 22 carbon atoms.

8. The combination of an organic polymer together with

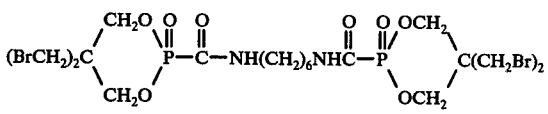

9. The combination of an organic polymer together with

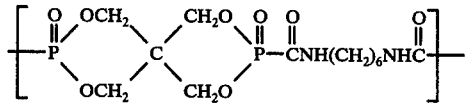

with —H and —NCO end groups, and having a degree of aggregation of 2 to 100, where R is selected from the group consisting of alkylene or alkyl substituted alkylenes of 2 to 20 carbon atoms, or arylene and alkyl substituted arylenes of 6 to 22 carbon atoms.

* * * * *